United States Patent [19]

Drahm

[11] Patent Number: 5,531,126
[45] Date of Patent: Jul. 2, 1996

[54] CORIOLIS-TYPE MASS FLOW SENSOR WITH FLOW CONDITION COMPENSATING

[75] Inventor: Wolfgang Drahm, Zwingen, Switzerland

[73] Assignee: Endress + Hauser Flowtec AG, Switzerland

[21] Appl. No.: 277,245

[22] Filed: Jul. 19, 1994

[30] Foreign Application Priority Data

Jul. 21, 1993 [EP] European Pat. Off. .............. 93810523

[51] Int. Cl.⁶ ................................................ G01F 1/84
[52] U.S. Cl. .................. 73/861.357; 73/861.356
[58] Field of Search ............................ 73/861.37, 861.38; 324/204, 202

[56] References Cited

U.S. PATENT DOCUMENTS

| | | | |
|---|---|---|---|
| 3,729,982 | 5/1973 | Senda . | |
| 4,422,338 | 12/1983 | Smith ................................... | 73/861.38 |
| 4,793,191 | 12/1988 | Flecken et al. ...................... | 73/861.38 |
| 4,801,897 | 1/1989 | Flecken ................................ | 73/861.38 |
| 4,949,583 | 8/1990 | Lang et al. ........................... | 73/861.37 |
| 5,253,533 | 10/1993 | Lam et al. ............................ | 73/861.37 |
| 5,321,991 | 6/1994 | Kalotay ................................ | 73/861.37 |
| 5,398,554 | 3/1995 | Ogawa et al. ....................... | 73/861.38 |

FOREIGN PATENT DOCUMENTS

| | | |
|---|---|---|
| 0473919 | 3/1992 | European Pat. Off. . |
| 4143361 | 3/1993 | Germany . |
| 0199922 | 8/1991 | Japan .................................. 73/861.38 |

OTHER PUBLICATIONS

Vögtlin et al., "Direct Measurement of Mass Flow Using the Coriolis Force", FLOWTEC AG Flow Measurement, Reinach (Switzerland), pp. 1–8, 1988.

*Primary Examiner*—Richard Chilcot
*Assistant Examiner*—Harshad Patel
*Attorney, Agent, or Firm*—Barnes & Thornburg

[57] ABSTRACT

This mass flow sensor is to be fitted with two straight tubes, but conventionally needed manifolds are to be dispensed with. The sensor can be installed, by flanges, in a conduit of a given diameter so as to be axially aligned with the conduit, through which flows a fluid to be measured. It has a straight measuring tube, which extends between the flanges and is traversed by the fluid, and a straight dummy tube, which extends parallel to the measuring tube and is not traversed by the fluid. Also provided are a nodal plate on the inlet side and a nodal plate on the outlet side, one of which fixes the inlet-side end portion of the measuring tube to the corresponding end portion of the dummy tube, and the other of which fixes the outlet-side end portion of the measuring tube to the corresponding end portion of the dummy tube, such that the measuring tube and the dummy tube are arranged side by side. A support tube has its ends fixed to the respective flanges. A circuit for exciting resonance vibrations of the measuring tube acts only on the dummy tube. The measuring tube and dummy tube may also be coaxial with one another.

8 Claims, 4 Drawing Sheets

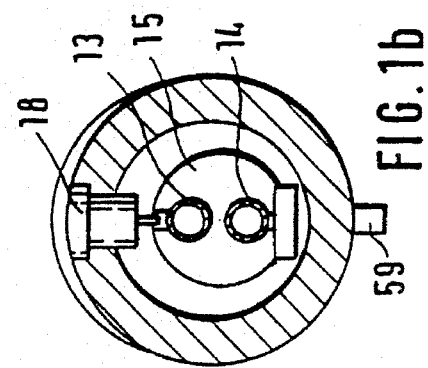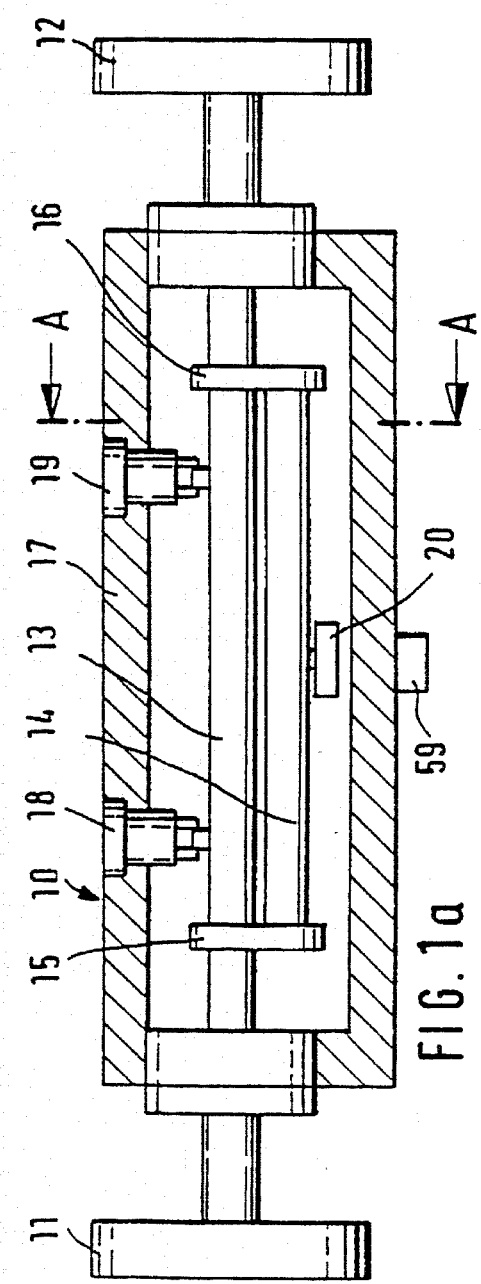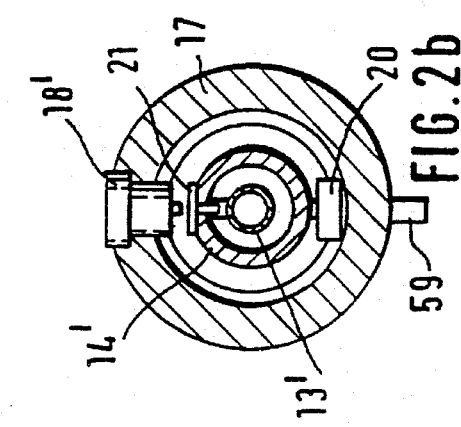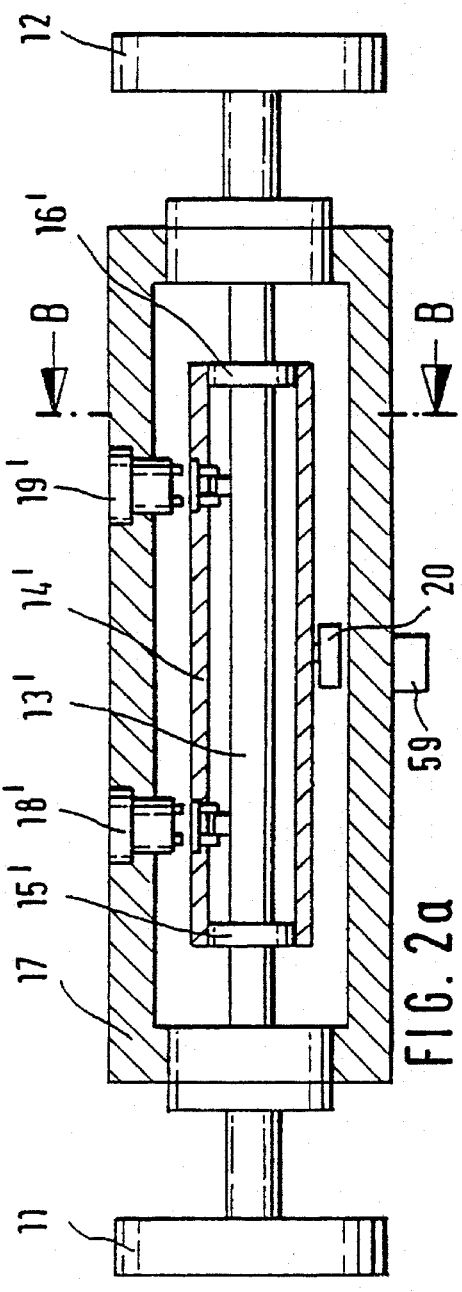

CORIOLIS-TYPE MASS FLOW SENSOR WITH FLOW CONDITION COMPENSATING

FIELD OF THE INVENTION

The present invention relates to a mass flow sensor working on the Coriolis principle, comprising a straight measuring tube as a vibrating body through which flows a fluid to be measured.

BACKGROUND OF THE INVENTION

Assignees own U.S. Pat. No. 4,793,191 describes a mass flow sensor which can be installed, by means of flanges, in a conduit of a given diameter so as to be axially aligned with said conduit, through which flows a fluid to be measured,
  with an inlet tube and an outlet tube,
    which serve to connect the mass flow sensor with the conduit,
  with an inlet manifold and an outlet manifold,
  with an external support tube
    whose ends are fixed to the inlet tube and outlet tube, respectively,
  with two annular diaphragms
    via which the inlet and outlet tubes are connected to the inlet manifold and outlet manifold, respectively,
  with two parallel, straight measuring tubes of the same inner diameter and the same wall thickness and each having its two ends fixed in the inlet manifold and outlet manifold, respectively, and
  with means which excite the measuring tubes into opposing resonance vibrations.

Furthermore, assignees own U.S. Pat. No. 4,949,583 describes a mass flow sensor with a single straight measuring tube which is excited into peristaltic vibrations of its cross-sectional area.

Mass flow sensors working on the above-mentioned principle with two straight measuring tubes vibrating in the manner of strings have proved to be effective in practice. However, for various reasons, e.g., because of the sensitivity of the mass flow sensor to vibrations stemming from the conduit or because of the dependence of the measurement result on the pressure of the fluid, the diaphragms cannot be made arbitrarily soft but must have a given minimum stiffness, so that the above influences cannot be completely suppressed.

Since, in addition, changes in the temperature of the fluid result in nonhomogeneous temperature distributions in the mass flow sensor, stress is caused in the vibrating straight measuring tubes and in the diaphragms. If this stress reaches values above the yield point of the diaphragms, irreversible plastic deformations are caused which irreversibly change the characteristics of the vibrating system, so that recalibration of the mass flow sensor will become necessary.

As further prior art shows, experts have been working on a solution to these problems for a long time. EP-A 473 919, for example, describes a mass flow sensor working on the Coriolis principle and forming part of a dosing mechanism
  which can be installed, by means of flanges, in a conduit of a given diameter through which flows a fluid to be measured,
  with a bent measuring tube extending between the flanges and traversed by the fluid,
  with a bent dummy tube extending parallel to the measuring tube and not traversed by the fluid,
  with the measuring tube and the dummy tube clamped in an internal supporting frame,
  with an external supporting frame, and
  with means which act only on the measuring tube to excite resonance vibrations of the measuring tube.

In this prior art mass flow sensor, the dummy tube serves as an antiresonantor, so that a tuned internal vibrating system consisting of measuring tube, antiresonator, and internal supporting frame is obtained. Its dimensions are calculated in advance by the finite-element method. Since, however, the resonance characteristics of the vibrating system depend primarily on the type of the fluid and also on the density and current temperature of the fluid, it is clear that a separate calculation has to be performed for each fluid, so that different results and, thus, different dimensions are obtained. For universal mass flow sensors which are to measure many different kinds of fluids, the proposal of EP-A 473 919 is therefore practically unsuitable.

DE-A 41 43 361 describes a mass flow sensor working on the Coriolis principle
  which can be installed, by means of flanges, in a conduit of a given diameter so as to be axially aligned with said conduit, through which flows a fluid to be measured,
  with a single straight, or substantially straight, measuring tube extending between the flanges and traversed by the fluid,
  with a support tube having its ends fixed to the respective flanges,
  with a compensation cylinder in which the measuring tube is fixed within the support tube and which does not touch the support tube,
  with means disposed between the measuring tube and the compensation cylinder for exciting resonance vibrations of the measuring tube, and
  with mass bodies mounted on the measuring tube to influence their natural frequency.

In this prior art mass flow sensor, the measuring tube is so installed in the compensation cylinder as to be under tensile stress at the normal temperature of the fluid. As the temperature rises, the tensile stress decreases due to the different expansion coefficients of compensation cylinder and measuring tube, and as the temperature rises further, the tensile stress turns into compressive stress. The upper temperature limit is therefore increased as compared with a measuring tube without tensile prestress.

Starting from U.S. Pat. No. 4,793,191, the first of the above references, it is an object of the invention to provide a mass flow sensor which is fitted with two straight tubes, but in which the manifolds and, thus, the diaphragms can be dispensed with and in which no compensating mass bodies are necessary on the measuring tube. Nevertheless, as far as possible, no vibrations are to be transmitted from the measuring tube to the support tube. Thus, a property of the mass flow sensor of U.S. Pat. No. 4,793,191, which is based there on the use of the diaphragms, is to be retained, but it is to be achieved in a different manner.

SUMMARY OF THE INVENTION

Accordingly, the invention consists in the provision of a mass flow sensor working on the Coriolis principle
  which can be installed, by means of flanges, in a conduit of a given diameter so as to be axially aligned with said conduit, through which flows a fluid to be measured,
  with a straight measuring tube extending between the flanges and traversed by the fluid, with a straight dummy tube extending parallel to the measuring tube and not traversed by the fluid, with a nodal plate on the inlet side and a nodal plate on the outlet side,
- one of which fixes the inlet-side end portion of the measuring tube to the corresponding end portion of the dummy tube, and
- the other of which fixes the outlet-side end portion of the measuring tube to the corresponding end portion of the dummy tube, so that the measuring tube and the dummy tube are arranged side by side, with a support tube having its ends fixed in the respective flanges, and with means which act only on the dummy tube to excite resonance vibrations of the measuring tube.

In a preferred embodiment of the invention, the dummy tube surrounds the measuring tube coaxially. In another embodiment of the invention, the dummy tube has its ends fitted in the respective nodal plates and is thereby closed, preferably evacuated.

In a further embodiment of the invention, the resonance frequency of the dummy tube is regulated so that the phase relationship between the vibration of the dummy tube and that of the measuring tube is 180° or as close as possible to this value.

In another embodiment of the invention, the means for exciting resonance vibrations comprise an electromagnetic system and a driver circuit, with the electromagnetic system containing
- a sleeve of soft magnetic material surrounding the dummy tube,
- a first electromagnet with a first U-shaped core and a first coil, and
- a second electromagnet with a second U-shaped core and a second coil,
  - said electromagnets being located diametrically opposite to each other with respect to the sleeve, and with the driver circuit generating an alternating current superposed on a direct current
- by applying a signal representative of the vibrations of the measuring tube to the first input of a phase comparator,
- by applying a signal generated from a signal representative of the vibrations of the dummy tube by means of an adjustable phase shifter to the second input of the phase comparator, and
- by integrating the output of the phase comparator,
  - with the adjustable phase shifter being adjusted until only minimum vibrations are detectable at the support tube, and
  - the alternating current being adjusted to the resonance frequency of the measuring tube by means of a phase-locked loop.

In a further embodiment of the invention, the means for exciting resonance vibrations comprise an electromagnetic system and a driver circuit, with the electromagnetic system containing
- a sleeve of soft magnetic material surrounding the dummy tube,
- a first electromagnet with a first U-shaped core and a first coil, and
- a second electromagnet with a second U-shaped core and a second coil,
  - the electromagnets being located diametrically opposite to each other with respect to the sleeve, and with the driver circuit applying positive half waves of a driver signal to the first electromagnet, and negative half waves of said signal to the second electromagnet, the driver signal being the output signal of a phase shifter
  - whose signal input is supplied with a signal representative of the vibrations of the measuring tube, and
  - whose control input is supplied with the integrated output signal of a phase comparator,
    - one input of which is supplied with the signal representative of the vibrations of the measuring tube, and
    - the other input of which is supplied with a signal representative of the vibrations of the dummy tube via an adjustable phase shifter,
  - the phase shifter being adjusted until only minimum vibrations are detectable at the support tube.

In a further embodiment of the invention, the means for exciting resonance vibrations comprise an electromagnetic system and a driver circuit, with the electromagnetic system containing
- a sleeve of soft magnetic mmaterial surrounding the dummy tube,
- a first electromagnet with a first U-shaped core and a first coil, and
- a second electromagnet with a second U-shaped core and a second coil, and
  - the electromagnets being located diametrically opposite to each other with respect to the sleeve, and with the driver circuit applying positive half waves of a driver signal to the first electromagnet, and negative half waves of said signal to the second electromagnet, the driver signal being the output signal of a voltage-controlled oscillator,
  - whose control input is supplied with the integrated output signal of a phase comparator,
    - one input of which is supplied with a signal representative of the vibrations of the measuring tube, and
    - the other input of which is supplied with a signal representative of the vibrations of the dummy tube via an adjustable phase shifter,
  - the phase shifter being adjusted until only minimum vibrations are detectable at the support tube.

In these three circuit embodiments of the invention, the adjustable phase shifter may be replaced by a sensor for measuring the acceleration of the support tube, and the phase comparator by a multiplier.

In a last embodiment of the invention, the viscosity of the fluid can be determined from the vibration amplitudes of measuring tube and dummy tube.

BRIEF DESCRIPTION OF THE DRAWINGS

The invention will now be explained in more detail with reference to the accompanying drawings, which are schematics of embodiments of the mechanical portion and different driver circuits.

FIG. 1 is a vertical longitudinal section of the mechanical portion of a mass flow sensor according to the invention;

FIG. 2 is a vertical longitudinal section of one embodiment of the mechanical portion of a mass flow sensor according to the invention;

DETAILED DESCRIPTION OF THE DRAWINGS

Figure 3:
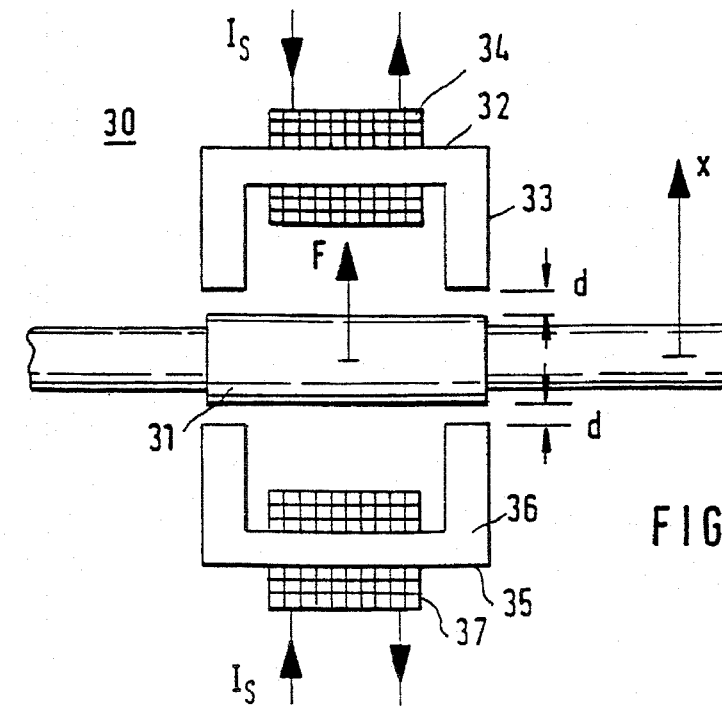
FIG. 3 shows schematically an electromagnetic system for exciting the dummy tube.

The mechanical portion of a mass flow sensor 10, shown in FIG. 1a in a longitudinal section and in FIG. 1b in a cross section taken along line A—A of FIG. 1a, can be installed, via flanges 11, 12, in a conduit of a given diameter through which flows a fluid to be measured, and which is not shown to simplify the illustration. The mechanical portion has a straight measuring tube 13, which is fixed at its ends in the respective flanges 11, 12.

Also provided is a straight dummy tube 14, which extends parallel to the measuring tube and is not traversed by the fluid, and which may be closed and preferably evacuated. Instead of a dummy tube, a solid rod of any section, preferably a cylindrical, particularly circular cylindrical rod, may be provided.

The dummy tube 14 is connected with the measuring tube 13 via a nodal plate 15 on the inlet side and a nodal plate 16 on the outlet side. The nodal plate 15 fixes the inlet-side end portion of the measuring tube 13 to the corresponding end portion of the dummy tube 14, and the nodal plate 16 fixes the outlet-side end portion of the measuring tube 13 to the corresponding end portion of the dummy tube 14, so that the measuring tube and the dummy tube 14 are arranged side by side.

FIG. 1 shows a preferred variation of this fixing, namely that the two ends of the dummy tube 14 butt-end in the respective nodal plates 15, 16, where they are fitted tight, particularly vacuum-tight, e.g., soldered or welded in.

The flanges 11, 12 are fixed in a support tube 17 in which are mounted two sensing elements 18, 19 with which the vibrations of the measuring tube 13 can be converted into electric measurement signals. These sensing elements may be, for example, optoelectronic sensors as are described in U.S. Pat. No. 4,801,897, or electromagnetic sensors as are explained, for example, in EP-A 83 144.

In operation, only the dummy tube 14 is excited, by suitable means, into resonance vibrations, which are transmitted via the nodal plates 15, 16 to the measuring tube 13, so that the latter is also excited into resonance vibrations, which are opposite to those of the dummy tube; hence, parts of the measuring tube and dummy tube which face toward each other vibrate toward or away from each other.

These means for exciting the resonance vibrations of the dummy tube comprise an electromagnetic driver arrangement 20 which is mounted on the dummy tube 14 midway between the flanges. The driver electronics may be, for example, of the type described in U.S. Pat. No. 4,801,897, which contains a phase-locked loop for automatic adjustment to the resonance frequency of vibrating tubes.

In operation, a phase difference of the vibrations of the inlet-side portion of the measuring tube 13 from those of the outlet-side portion of this tube is measured by means of the sensing elements 18, 19 and associated evaluation electronics which determine the mass flow rate of the fluid from the phase difference and/or the density of the fluid from the vibration frequency of the measuring tube 13. Evaluation electronics for the above-mentioned optoelectronic sensors are described, for example, in the journal "Automatisierungstechnische Praxis atp", 1988, No. 5, pages 224 to 230.

The mechanical portion of another embodiment of the invention, shown in FIG. 2a in a longitudinal section and in FIG. 2b in a section taken along line B—B of FIG. 2a, differs from the embodiment of FIG. 1 in that the measuring tube 13' and the dummy tube 14' are not arranged side by side but are coaxial with one another, with the measuring tube 13' inside and the dummy tube 14' outside.

Here, too, the nodal plates 15', 16' preferably form tight closures of the dummy tube 14'. Particularly suitable sensing elements 18', 19' are the above-mentioned optical sensors, since it is readily possible to enable a light signal to pass through the wall of the dummy tube 14' by putting, e.g., sealing, a window of a vitreous material into this wall.

The other parts of the arrangement of FIG. 2 are identical to the corresponding parts of FIG. 1, so that reference can be made to their above description.

The nodal plates 15, 15', 16, 16', besides being fixed to the measuring tube and the dummy tube as described, may also be attached to the support tube 17, 17'.

On the support tubes 17 of FIGS. 1a and 2a, preferably in the middle thereof, a sensing element 59 may be provided for measuring the acceleration of the respective support tube, this sensor being of interest in connection with the driver circuits explained below with reference to FIGS. 4 to 7.

FIG. 3 shows schematically an electromagnetic system 30 for exciting the dummy tube 14, 14'. The electromagnetic system 30 includes a sleeve 31 of soft magnetic material, such as soft iron, which surrounds the dummy tube. Furthermore, a first electromagnet 32 with a first U-shaped core 33 and a first coil 34 as well as a second electromagnet 35 with a second U-shaped core 36 and a second coil 37 are provided. The two electromagnets 32, 35 are located diametrically opposite to each other with respect to the sleeve 31, and thus also with respect to the dummy tube 14, 14'.

The force F(x) in the X-direction, which is indicated in FIG. 3, is dependent on the coil current $I_S$, which flows through the coils 36, 37, and on the air gap d according to the following equation:

$$F(x) = 0.5 \mu_0 I_S^2 w^2 A [1/(d-x)^2 - 1/(d+x)^2],$$

where $\mu_0$=permittivity (=1.256*10$^{-8}$ Vs/Acm)

w=number of turns of a coil

A=cross section through which passes the magnetic field of the coil, i.e., essentially the end areas of the two legs of the U.

The two coils 34, 37 are supplied alternately with the half wave of an alternating current i, preferably a sine-wave current, from a driver circuit. The necessary 90° phase lead between this alternating current i and the tube vibration is generated within the driver circuit.

To ensure that the measuring tube 13, 13' and the dummy tube 14, 14' vibrate oppositely to each other, i.e., practically in phase opposition, and that no vibrations are transmitted to the support tube 17, a direct current I is superposed on the alternating current i. The coil current $I_S$ therefore is $$I_S = i + I.$$

Through the superposition of the regulated direct current I, the resonance frequency of the dummy tube 14, 14' can be changed, since the direct current I causes the electromagnetic system 30 to behave like an electrical spring of adjustable tension.

To simplify further calculations, the above equation for F(x) can be replaced by a linear equation as follows, without introducing an intolerable error:

$$F'(x)=0.5\mu_0 I_s^2 w^2 A k x,$$

where k is a constant with the dimension "length$^{-3}$", which follows from the concrete dimensioning.

Looking at the action of the force caused by the direct current I, one can see that the direction of the force coincides with that of the deflection x, with the magnitude of the force being proportional to the direct current I. By contrast, mechanical springs exert a force which counteracts their deflection. The spring constant $c_e$ of the electrical spring considered here is therefore negative.

To determine the necessary spring constant $c_e$, account is taken of the fact that the electrical spring is connected in parallel with the mechanical spring system constituted by the vibrating dummy tube, which has the spring constant $c_m$.

If the resonance frequency $f_{res}$ of the dummy tube, which has a mass m, is to be changed by a difference frequency $\delta f$ by means of the electrical spring, i.e., the direct current I, then $$c_e = -[c_m - 4m\pi^2 (f_{res} - \delta f)^2]$$

To enhance the performance and improve the linearity of the electromagnetic system 30, the respective core 33, 36 may be, at least in part, a permanent magnet which produces a constant magnetic flux, so that for the respective coil 34, 37, the magnetic flux can be increased or reduced in dependence on the current $I_S$ and the direction of this current.

Figure 4:
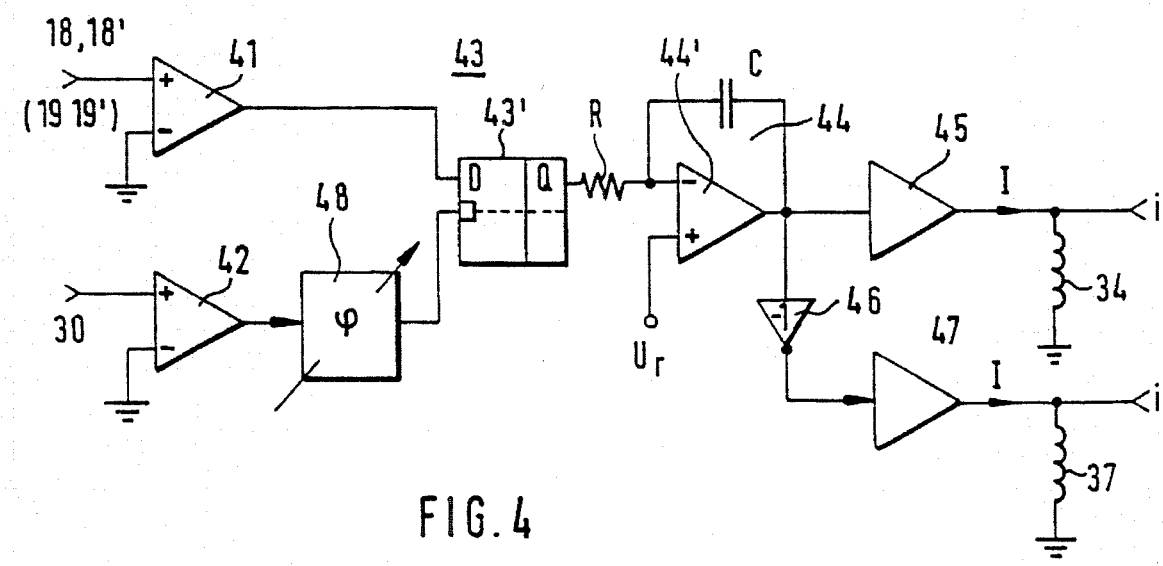
FIG. 4 is a block diagram of a portion of a first driver circuit for the electromagnetic system of FIG. 3.

A circuit for generating the direct current I is shown in block-diagram form in FIG. 4. This circuit is regarded here as a portion of the above-mentioned driver circuit, which generates the alternating current i.

As shown in FIG. 4, the signal from one of the sensing elements 18, 18' or 19, 19', i.e., a signal representative of the vibrations of the measuring tube 13, 13', is applied to the noninverting input of a differential amplifier 41. A voltage obtained from one of the coils 34, 37 of the electromagnetic system 30, i.e., a signal representative of the vibrations of the dummy tube 14, 14', is applied to the noninverting input of a differential amplifier 42.

Instead of taking the signal representative of the vibrations of the dummy tube 14, 14' from the electromagnetic system 30, a vibration sensor (not shown) may be mounted on the dummy tube 14, 14'.

The adjustable phase shifter 48 is adjusted, e.g., during in-shop calibration of the mass flow sensor, until practically no vibrations are detectable at the support tube 17, i.e., until these vibrations have decreased to a minimum.

Because of this adjustment to the vibration minimum of the support tube, measuring tube 13, 13' and dummy tube 14, 14' also vibrate with the phase difference φ set at the adjustable phase shifter 48. This phase difference is due to constructional parameters and represents an instrument constant.

Because of the combination of the signals by means of the D flip-flop 43', which as mentioned, acts as a phase comparator, the desired (180°−φ) phase relationship is obtained between dummy tube 14, 14' and measuring tube 13, 13', as is readily apparent: The duration of the pulses at the output of the D flip-flop 43' determines the numerical value of the direct current I.

Figure 5:
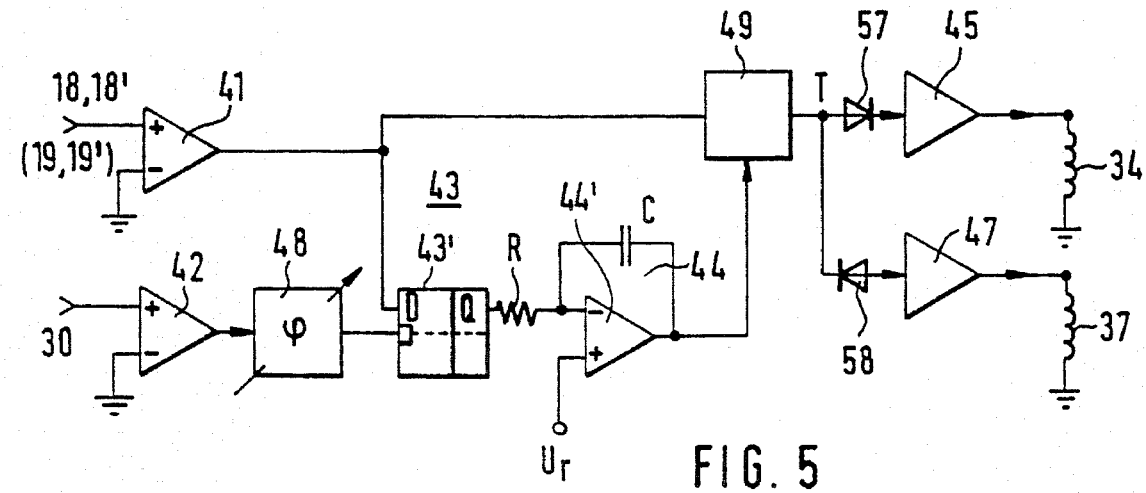
FIG. 5 is a block diagram of a portion of a second driver circuit for the electromagnetic system of FIG. 3.

Another circuit for energizing the coils 34, 37 is shown in block-diagram form in FIG. 5. Parts having the same functions as in FIG. 4 are designated by the same reference characters and will not be explained again.

Instead of the superposition of the direct current I and the alternating current i as in FIG. 4, positive and negative half waves of a driver signal T are utilized here; the positive half waves are applied to the first electromagnet 32, and the negative half waves to the second electromagnet 35.

The driver signal T is the output signal of a phase shifter 49, whose signal input is connected to the output of the differential amplifier 41 and thus receives the signal representative of the vibrations of the measuring tube 13, 13'. The control input of the phase shifter 49 is supplied with the integrated output signal from a phase comparator 43, namely with the output signal from the D flip-flop 43' integrated by the integrator 44.

Diodes 57, 58 are connected in inverse parallel between the output of the phase shifter 49 and the respective inputs of the power stages 45, 47. Thus the power stage 45 is fed only with positive half waves of the output of the phase shifter 49, and the power stage 47 with negative half waves.

The driver circuit of FIG. 5, together with the dummy tube, is self-exciting, i.e., the phase-locked loop required in FIG. 4 to generate the alternating current i is not necessary in FIG. 5. This represents, among other things, a cost advantage.

Figure 6:
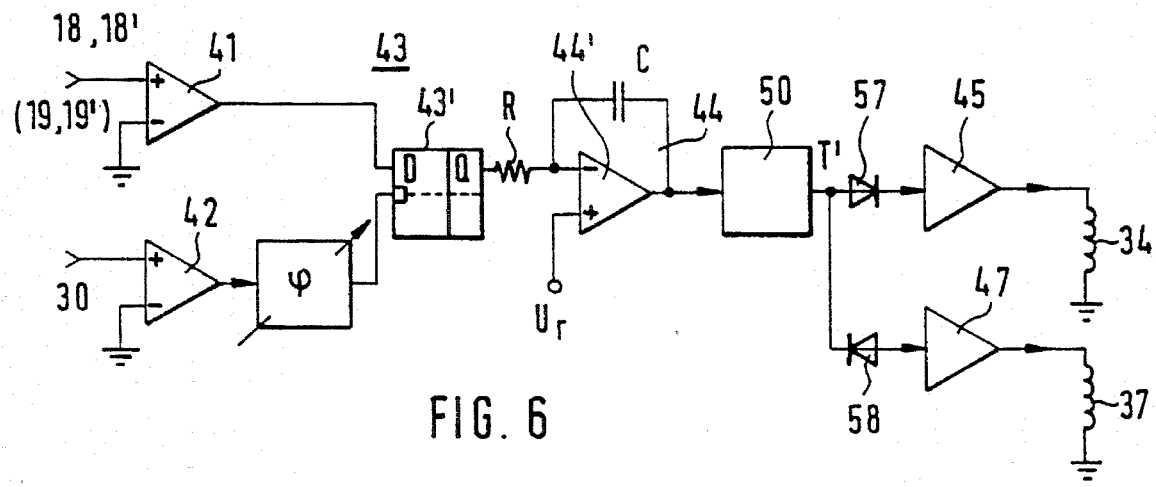
FIG. 6 is a block diagram of a portion of a third driver circuit for the electromagnetic system of FIG. 3.

A further circuit for energizing the coils 34, 37 is shown in block-diagram form in FIG. 6; it is a modification of the driver circuit of FIG. 5. Parts having the same functions as in FIG. 5 are designated by like reference characters and will not be explained again.

In FIG. 6, too, instead of the superposition of the direct current I and the alternating current i as in FIG. 4, positive and negative half waves of a driver signal T' are utilized. The driver signal is provided not by a phase shifter as in FIG. 5, but by a voltage-controlled oscillator 50, whose control input receives the integrated output signal of a phase comparator 43, namely the output signal of the D flip-flop 43' integrated by the integrator 44.

Figure 7:
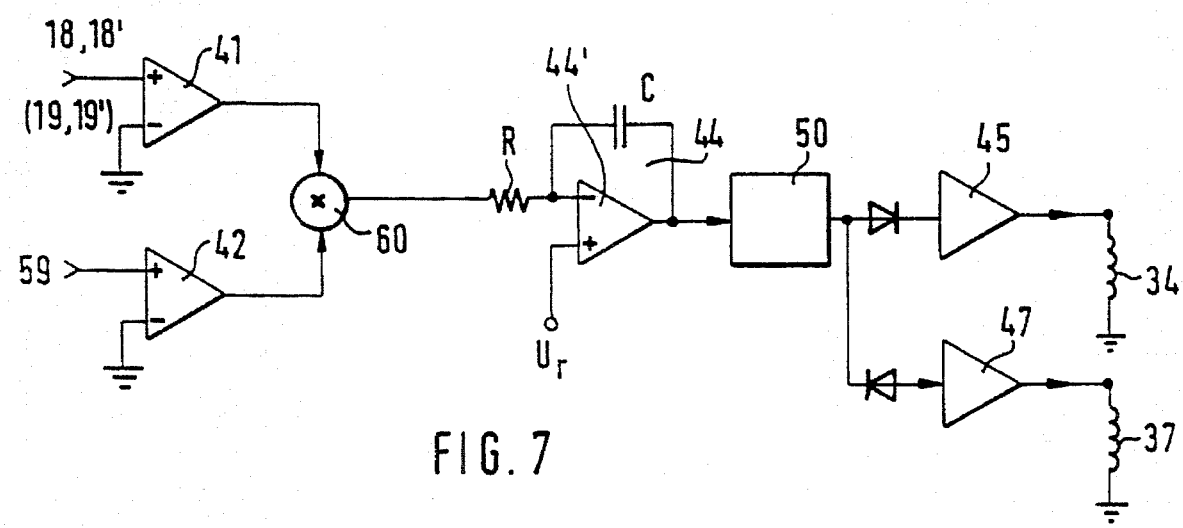
FIG. 7 is a block diagram of a portion of a further development of the driver circuits for the electromagnetic system of FIG. 3.

Still another circuit for energizing the coils 34, 37 is shown in block-diagram form in FIG. 7. FIG. 7 is a development of the driver circuits of FIGS. 5 and 6. Parts in FIG. 7 corresponding to parts in FIG. 6 are designated by like reference characters and will not be explained again.

In FIG. 7, the adjustable phase shifter 48 of FIGS. 4, 5, and 6 has been replaced with a sensing element 59 for measuring the acceleration of the support tube 17, and the phase comparator 43, comprising the D flip-flop 43', has been replaced with a multiplier 60. This eliminates the need for manually adjusting the vibration minimum at the support tube; this minimum adjusts itself automatically. This replacement is also possible within the circuit of FIG. 4.

In the embodiments of FIGS. 5 to 7, an electrodynamic system, which consists of a permanent magnet and a moving coil, can be used instead of the electromagnetic system 30.

Figure 8:
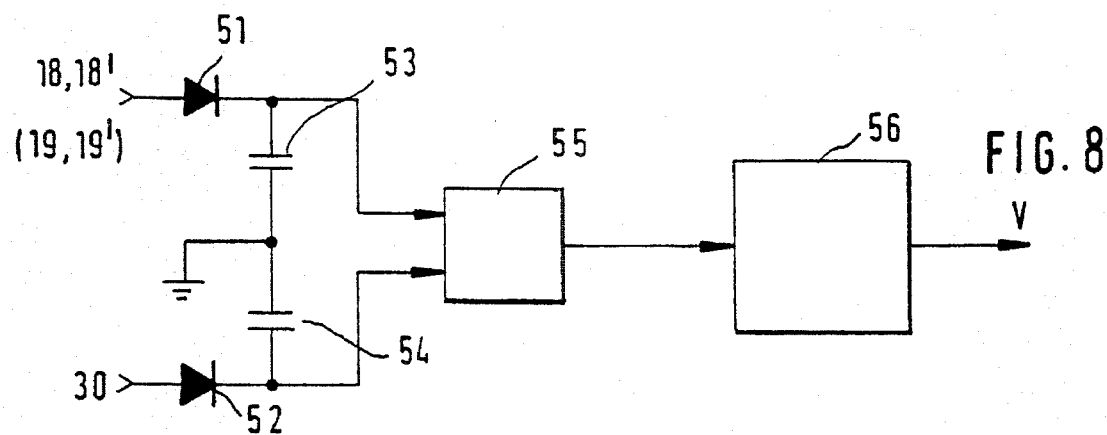
FIG. 8 is a block diagram of a circuit for measuring the viscosity of the fluid.

The arrangement according to the invention can also be used to determine the viscosity of the fluid. This is done with the circuit of FIG. 8. The signal from one of the sensing elements 18, 18' or 19, 19' and a signal provided by the driver circuit and representative of the vibration amplitude of the dummy tube 14, 14', e.g., the above-mentioned signal from the electromagnetic system 30, are peak-value-rectified by means of diodes 51 and 52 with associated capacitors 53 and 54, respectively. The output signal of the diode 51 is divided by the output signal of the diode 52 by means of an analog divider 55. The output signal of the divider 55 is converted to the viscosity signal V by means of a microcontroller 56. To this end, the microcontroller 56 may contain a look-up table which contains a previously stored assignment between the output-signal values of the divider 55 and the viscosity V.

I claim:

1. A mass flow sensor working on the Coriolis principle
   having flanges for installing said flow sensor in a conduit of a given diameter so as to be axially aligned with said conduit, through which flows a fluid to be measured,
   with a straight measuring tube having an inlet-side and an outlet-side end portions and extending between the flanges and traversed by the fluid,
   with a straight dummy tube extending parallel to the measuring tube, defined by end portions and not traversed by the fluid,
   with a nodal plate on the inlet side of said measuring tube and a nodal plate on the outlet side of said measuring tube,
      one of which fixes the inlet-side end portion of the measuring tube to the corresponding end portion of the dummy tube, and
      the other of which fixes the outlet-side end portion of the measuring tube to the corresponding end portion of the dummy tube, so that the measuring tube and the dummy tube are arranged side by side,
   with a support tube having its ends fixed in the respective flanges, and
   with means which act only on the dummy tube to excite resonance vibrations of the measuring tube so that the phase relationship between the vibration of the dummy tube and that of the measuring tube is 180 or as close as possible to this value.

2. A mass flow sensor as claimed in claim 1, comprising said dummy tube surrounding the measuring tube coaxially.

3. A mass flow sensor as claimed in claim 1 or 2, comprising said dummy tube having its ends fitted in the respective nodal plates, the dummy tube thus being closed, preferably evacuated.

4. A mass flow sensor as claimed in claim 1 wherein the means for exciting resonance vibrations comprise an electromagnetic system and a driver circuit,
   with the electromagnetic system containing
      a sleeve of soft magnetic material surrounding the dummy tube,
      a first electromagnet with a first U-shaped core and a first coil, and
      a second electromagnet with a second U-shaped core and a second coil,
         the electromagnets being located diametrically opposite to each other with respect to the sleeve, and
   with the driver circuit generating an alternating current superposed on a direct current
      by applying a signal represenative of the vibrations of the measuring tube to the first input of a phase comparator,
      by applying a signal generated from a signal representative of the vibrations of the dummy tube by means of an adjustable phase shifter to the second input of the phase comparator, and
      by integrating the output of the phase comparator,
         with the adjustable phase shifter being adjusted until only minimum vibrations are detectable at the support tube, and
      the alternating current being adjusted to the resonance frequency of the measuring tube by means of a phase-locked loop.

5. A mass flow sensor as claimed in claim 1 wherein the means for exciting resonance vibrations comprise an electromagnetic system and a driver circuit
   with the electromagnetic system containing
      a sleeve of soft magnetic material surrounding the dummy tube,
      a first electromagnet with a first U-shaped core and a first coil, and
      a second electromagnet with a second U-shaped core and a second coil,
         the electromagnets being located diametrically opposite to each other with respect to the sleeve, and
   with the driver circuit applying positive half waves of a driver signal to the first electromagnet, and negative half waves of said signal to the second electromagnet,
      the driver signal being the output signal of a phase shifter,
         whose signal input is supplied with a signal representative of the vibrations of the measuring tube, and
         whose control input is supplied with the integrated output signal of a phase comparator,
            one input of which is supplied with the signal representative of the vibrations of the measuring tube, and
            the other input of which is supplied with a signal representative of the vibrations of the dummy tube via an adjustable phase shifter,
         the phase shifter being adjusted until only minimum vibrations are detectable at the support tube.

6. A mass flow sensor as claimed in claim 1 wherein the means for exciting resonance vibrations comprise an electromagnetic system and a driver circuit
   with the electromagnetic system containing
      a sleeve of soft magnetic material surrounding the dummy tube,
      a first electromagnet with a first U-shaped core and a first coil, and
      a second electromagnet with a second U-shaped core and a second coil,
         the electromagnets being located diametrically opposite to each other with respect to the sleeve, and
   with the driver circuit applying positive half waves of a driver signal to the first electromagnet, and negative half waves of said signal to the second electromagnet,
      the driver signal being the output signal of a voltage-controlled oscillator,
         whose control input is supplied with the integrated output signal of a phase comparator,
            one input of which is supplied with a signal representative of the vibrations of the measuring tube, and
            the other input of which is supplied with a signal representative of the vibrations of the dummy tube via an adjustable phase shifter,
         the phase shifter being adjusted until only minimum vibrations are detectable at the support tube.

7. A mass flow sensor as claimed in any one of claims 4 to 6 wherein the adjustable phase shifter is replaced with a sensor for measuring the acceleration of the support tube, and the phase shifter with a multiplier.

8. A mass flow sensor as claimed in claim 1 wherein the viscosity of the fluid is determined from the vibration amplitudes of measuring tube and dummy tube.

* * * * *